United States Patent [19]
Ratliff

[11] Patent Number: 5,284,130
[45] Date of Patent: Feb. 8, 1994

[54] SURGICAL INSTRUMENT POSITIONING AND SECURING APPARATUS

[76] Inventor: Jack L. Ratliff, 739 Hayne Ave., Aiken, S.C. 29801

[21] Appl. No.: 893,329

[22] Filed: Jun. 3, 1992

[51] Int. Cl.⁵ .............................................. A61B 17/02
[52] U.S. Cl. .................................. 128/20; 248/160; 248/278; 606/1
[58] Field of Search ............... 128/20, 17, 3, 18; 606/1, 54, 57; 248/104, 160, 276, 278, 299

[56] References Cited

U.S. PATENT DOCUMENTS

| | | | |
|---|---|---|---|
| 3,096,962 | 7/1963 | Meijs | 248/276 |
| 4,143,652 | 3/1979 | Meier et al. | 128/20 |
| 4,239,036 | 12/1980 | Krieger | 128/20 |
| 4,573,452 | 3/1986 | Greenberg | 128/20 |
| 4,863,133 | 9/1989 | Bonnell | 248/278 |
| 4,867,404 | 9/1989 | Harrington et al. | 128/20 X |
| 5,037,053 | 8/1991 | Fox et al. | 248/278 |

Primary Examiner—Richard J. Apley
Assistant Examiner—Donna L. Maraglio
Attorney, Agent, or Firm—Dority & Manning

[57] ABSTRACT

An apparatus is provided for securing a surgical instrument at a predetermined attitude and at a predetermined location about an operating table. The apparatus includes instrument gripping means pivotally mounted upon a flexible column, which in turn is pivotally mounted upon locking means configured to slide about an operating table positioning bar. Tensioning means are provided in operative communication with the instrument gripping means, the flexible column and the locking means. Upon actuation of the tensioning means, the instrument gripping means securely grasps a surgical instrument at a predetermined attitude relative the operating table, the flexible column rigidifies in a predetermined posture and the locking means become non-movable relative the positioning bar.

14 Claims, 3 Drawing Sheets

SURGICAL INSTRUMENT POSITIONING AND SECURING APPARATUS

BACKGROUND OF THE INVENTION

The present invention relates to an apparatus for positioning and securing surgical instruments around an operating table and more particularly to a device for the near automatically securing of surgical instruments in an array evolving with the surgeon's need as the procedure progresses.

Medical technology has progressed to the point where certain internal (within the body cavity) surgical operations are now performed remotely from outside the body cavity. No longer is it necessary to lay open the patient's body, for instance, to remove the patient's gallbladder. Today many of these operations are performed remotely with a telescope (called an endoscope for any optical video instruments looking inside of the body). An endoscope is inserted through a tiny incision and extended into the critical area, thereby allowing a surgeon to view the operation remotely from outside the body with, for example, a television screen. The instruments are inserted into the abdomen or body through tiny surgical incisions. The surgeon can then manipulate the endoscopic instruments from outside the body cavity while watching the procedure on the television screen.

Although the concept of remote endoscopically monitored instrumentation has greatly reduced patient recovery time, the technique is extremely labor intensive and requires a team of highly trained professionals.

With a typical gallbladder operation, four or more such instruments are commonly inserted into a patient's abdomen. A large amount of coordination is required to properly manipulate and position them. One surgeon or trained team member must continually reposition the endoscopic video camera to keep both internal organs and instruments safely and effectively in perspective. Without this coordinated, continually moving support, the surgeon is "blind" and his helpers have no way of coordinating their efforts. Another surgeon, or highly trained medical technician, must hold perfectly still certain of the retractor instruments while the primary surgeon manipulates the "active operating instrument".

In a typical gallbladder operation, one of the instruments is the endo-television camera, a second instrument is either a dissecting laser or electric cautery probe, while the other two instruments are normally retractor devices. Two of the retractor devices are used to grasp and pull the gallbladder aside to a position where the surgeon can reach the "roots" of the gallbladder with the dissector. Traditionally a surgeon or other technician must maintain effective video surveillance while another holds the two retractors securing the gallbladder completely still and the primary surgeon removes the gallbladder with the operating (dissecting) instrument.

Various surgical retaining devices have been developed to hold surgical instruments firmly in some desired attitude or posture. These devices, however, are fairly cumbersome, often project awkwardly into the work area, and are generally not "user friendly" enough to significantly reduce the time and/or number of skilled personnel required to perform present day remote endoscopic surgery. These devices include U.S. Pat. No. 3,572,326 to Jensen and U.S. Pat. No. 4,355,631 to LaVahn. U.S. Pat. Nos. 4,616,632 to Wigoda; 3,858,578 to Milo; and 3,638,973 to Poletti disclose fluid actuated joint means for elements of a retractor.

In an ideal situation, a single surgeon should be able to manipulate and position the array of endoscopic surgical instruments with the aid of fewer highly trained personnel. The obligate new mechanism must be user friendly requiring essentially no continual set up time. It must be low profile and flexible enough to stay out of the way while securing a variety of instruments in the almost fluid evolution or progression of the surgical procedure so that the procedure is faster and safe. This would significantly reduce the size of an operating team and thus, the cost of the operation to the patient. It would significantly reduce the length of time required for such procedures allowing either more extensive surgery in the same time frame or less anesthesia to accomplish the same current goals. Thus the safety to the patient would be dramatically increased.

The present surgical instrument securing devices generally do not achieve these goals.

OBJECTS AND SUMMARY OF THE INVENTION

It is a principal objective of the present invention to provide an apparatus for positioning and securing surgical instruments, such as a retractor.

A further principal object of the present invention is to provide an automatic surgical instrument securing apparatus suitable for use with modern day endoscopic surgical techniques.

It is also a principal object of the present invention to provide an apparatus which allows a surgeon to simultaneously locate a surgical instrument anywhere around an operating table while positioning the instrument into some desired attitude or posture within the patient's body cavity.

Yet a further principal object of the present invention is to provide a surgical instrument positioning and securing apparatus which can be controlled hands-free thereby providing the surgeon with free mobility of his hands to conduct the operation more rapidly and safely.

A still further principal object of the present invention is to provide an apparatus which reduces the necessity for additional highly skilled medical personnel in an operating room to perform routine operating tasks.

Yet another principal object of the present invention is to provide a surgical instrument securing device which greatly reduces the degree of coordination required between a surgical team.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an apparatus for selectively positioning a surgical instrument relative to an operating table is provided. The apparatus of the present invention comprises a compressible flexible column having opposite ends and defining a path therethrough; instrument gripping means are provided for securely holding a surgical instrument at a predetermined attitude, the gripping means are pivotally mounted to one end of the flexible column so that a frictional interface exists between the instrument gripping means and the flexible column, the instrument gripping means also defines an opening therethrough; locking means pivotally mounted to the other end of the flexible column so that a frictional interface exists between the locking means and the flexible column, the locking means defining a path therethrough alignable with the flexible column path and the instrument gripping means opening, the locking means configured to slide along an operating table positioning bar; tensioning means for compressing the instrument gripping means, the flexible column, and the locking means together, the tensioning means running through the instrument gripping means opening, the flexible column path, and the locking means path so that upon actuation of the tensioning means, the instrument gripping means securely grips and holds a surgical instrument at some predetermined attitude, the flexible column assumes a rigid posture, and the locking means maintains a preselected position on the operating table positioning bar; and an actuation device in operative communication with the tensioning means for actuating and releasing the tensioning means.

In one preferred embodiment of the invention, the instrument gripping means comprises a pivotal head having a pivotal frictional interface with the flexible column and defining a recessed instrument seating surface within which surgical instruments are carried; and a clamping device for securing a surgical instrument within the recessed seating surface, the clamping device being physically connected with the tensioning means so that upon actuation of the tensioning means the clamping device non-movably secures the surgical instrument against the pivotal head with the pivotal head in turn being non-movably secured against the flexible column at a predetermined attitude relative to the flexible column.

The flexible column according to the present invention may preferably comprise a plurality of stacked segments having freely rotatable frictional interfaces between each of the segments so that each segment is freely rotatable relative an adjacent segment. The segments are further configured so that upon being compressed together the segments non-movably secure against each other causing the flexible column to rigidify in some desired posture.

In one preferred embodiment of this invention, the locking means comprises a device having an upper portion and a lower portion, the respective portions define a recessed groove configured for receiving the operating table positioning bar so that the locking means in an uncompressed state may slide along the positioning bar, and whereupon being compressed together, the upper portion and the lower portion non-movably secure, or "lock," upon the positioning bar and secure the locking means at a predetermined location on the positioning bar relative to the operating table.

In yet another preferred embodiment of the invention, the tensioning means may comprise a cable with one end thereof attached within the instrument gripping means to the instrument clamping device, the cable running through the flexible column path and the locking means path; a piston assembly mounted to the locking means, the piston assembly including a piston within a cylinder, the other end of the cable being attached to the piston; and a pressure source disposed in communication with the top of the piston so that upon pressurization from the pressure source, the piston is forced to travel within the cylinder and thereby pulls the instrument gripping means, the flexible column, and the locking means together, and so that upon subsequent venting of the cylinder, the gripping means, the flexible column, and the locking means are permitted to relax and separate from each other. In one preferred embodiment of the invention, the pressure source may comprise a pressurized gas source, such as an operating room service pressurized air system.

The actuation device of the present invention may comprise a foot pedal in operative communication with a gas valve, the gas valve being configured to direct pressurized gas from the pressure source into communication with the top of the piston when the foot pedal is unactuated (not depressed), and to vent the pressurized gas from the cylinder upon actuating of the foot pedal.

In further accordance with the objects of the present invention, an apparatus for selectively positioning a surgical instrument relative to an operating table is provided. The apparatus comprises a positioning bar capable of being disposed generally around an operating table; a plurality of retractor holding devices slidably mountable upon the positioning bar so that each retractor holding device may be positioned at a predetermined location along the positioning bar.

Each retractor holding device further comprises a pivotally flexible column, the column defining a path therethrough; a retractor gripping means pivotally mounted to one end of the flexible column for securely holding a surgical retractor at some desired attitude, the retractor gripping means defining an opening therein alignable with the flexible column path; and a positioning bar locking device pivotally mounted to the other end of the flexible column for securing the retractor holding device to the positioning bar at a predetermined location, the positioning bar locking device defining a path therethrough alignable with the flexible column path.

The apparatus of this embodiment may further include tensioning means in operative communication with each retractor holding device for simultaneously activating the retractor gripping means and the positioning bar locking means of each retractor holding device, and for causing the flexible column of each retractor holding device to rigidify in some predetermined posture; and at least one manual actuation device in operative communication with the tensioning means and configured to actuate the tensioning means.

The apparatus of the present invention is particularly suited for securing and positioning telescopic surgical instruments which are used, for example, in endoscopic surgery. The apparatus allows a surgeon to position the instruments at a predetermined location around the operating table and at some desired attitude relative to the patient. The instruments can be inserted into the patient, for example through incisions in the abdominal wall, to accomplish their specific function while being secured in place by the apparatus of the present invention. The apparatus of the present invention is particularly suited for gallbladder removal operations.

The accompanying drawings, which are incorporated in and constitute a part of this specification, illustrate one embodiment of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures, in which.

Figure 1:
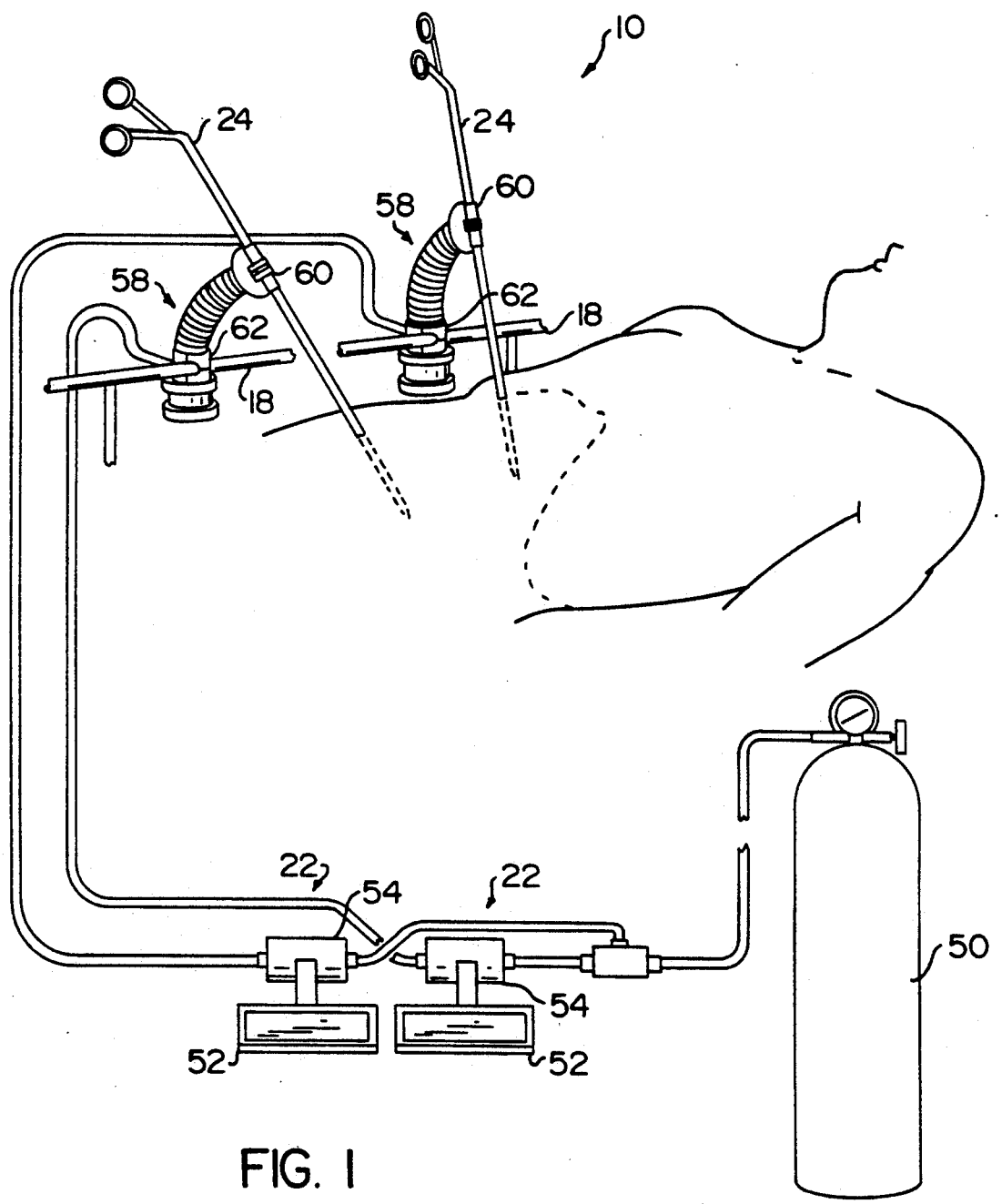
FIG. 1 is a schematic representation of one embodiment of the present invention.

Repeat use of reference characters in the following specification and appended drawings is intended to represent the same or analogous features, elements, or steps of the present invention.

DETAILED DESCRIPTION OF THE PREFERRED EMBODIMENTS

Reference now will be made in detail to the present preferred embodiments of the present invention, one or more examples of which are illustrated in the accompanying drawings. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover the modifications and variations of this invention provided they come within the scope of the appended claims and their equivalents.

In accordance with the invention, an apparatus for selectively positioning a surgical instrument relative to an operating table is provided. A preferred embodiment of the present invention is shown in FIG. 1 and is generally designated by the numeral 10. Apparatus 10 may be employed for positioning any variety of surgical instruments, such as retractors or the like. Apparatus 10 is particularly suited for securing and positioning telescopic surgical instruments such as those used in modern endoscopic surgery. For example, a routine endoscopic gallbladder operation may require the insertion of four or more endoscopic instruments through a patient's abdominal wall. Two of these instruments are normally retractors for pulling and holding the gallbladder in some position required by the surgeon which enables him to operate on the gallbladder. Apparatus 10 is well suited for positioning and securing these two retractors in a steady-state secure position without the necessity of having another surgeon or a skilled operating room technician hold the instruments.

In accordance with the apparatus of the present invention, a compressible flexible column having opposite ends is provided. As embodied herein and shown for example in FIGS. 2 and 3, a compressible flexible column is indicated generally by the numeral 12 and further defines an opening 13 therethrough. Column 12 is "flexible" in that it may be manipulated or posed by the surgeon into any desired posture. For example, column 12 may be curved or posed towards the patient or away from the patient depending on the surgeon's needs at the time.

Figure 2:
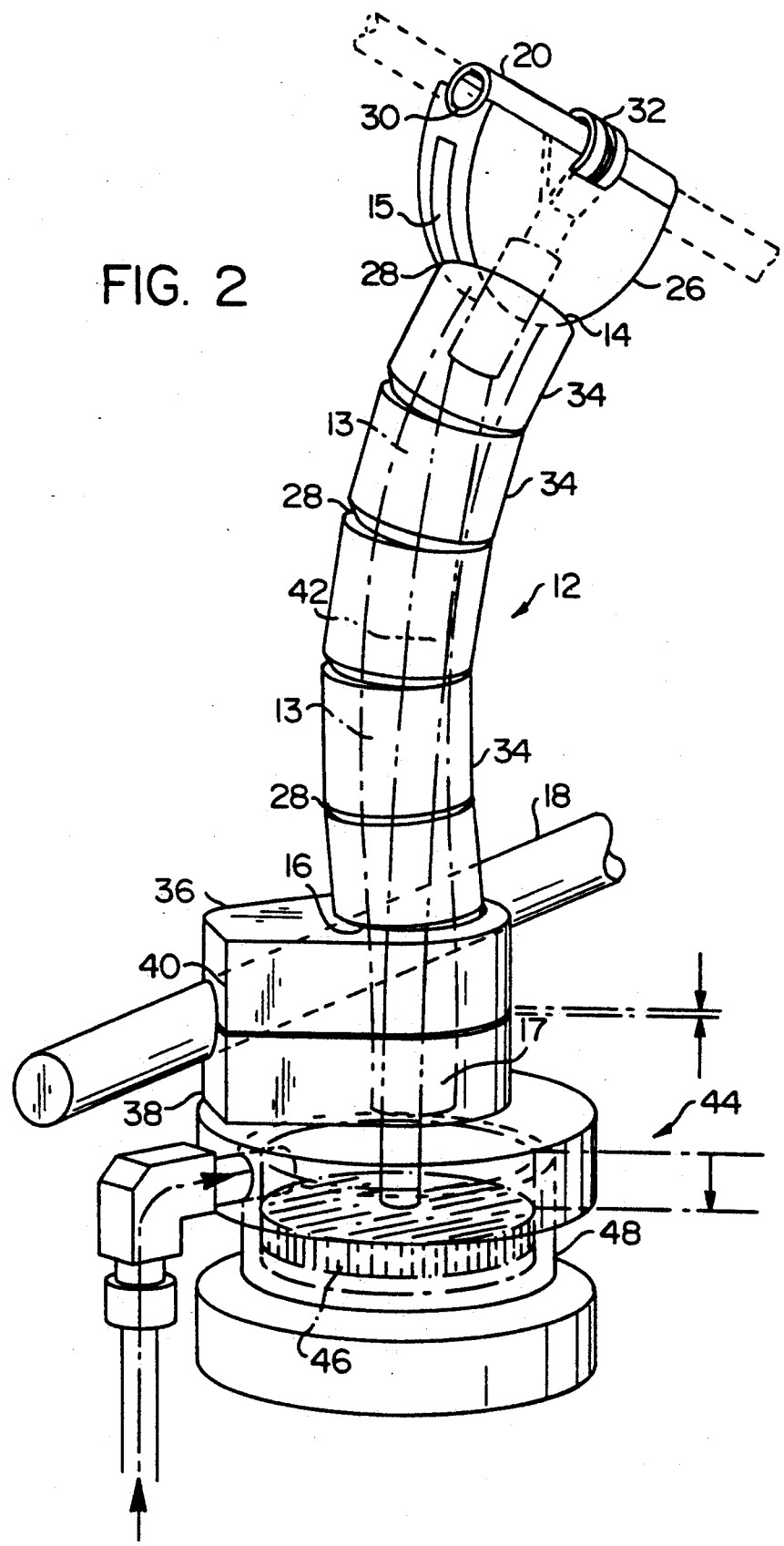
FIG. 2 is an enlarged perspective view (with portions shown in phantom by dashed lines and portions removed or cut away for ease of viewing) of the retractor holding devices illustrated in FIG. 1, the retractor holding device is shown in its compressed or rigidified state.
Figure 3:
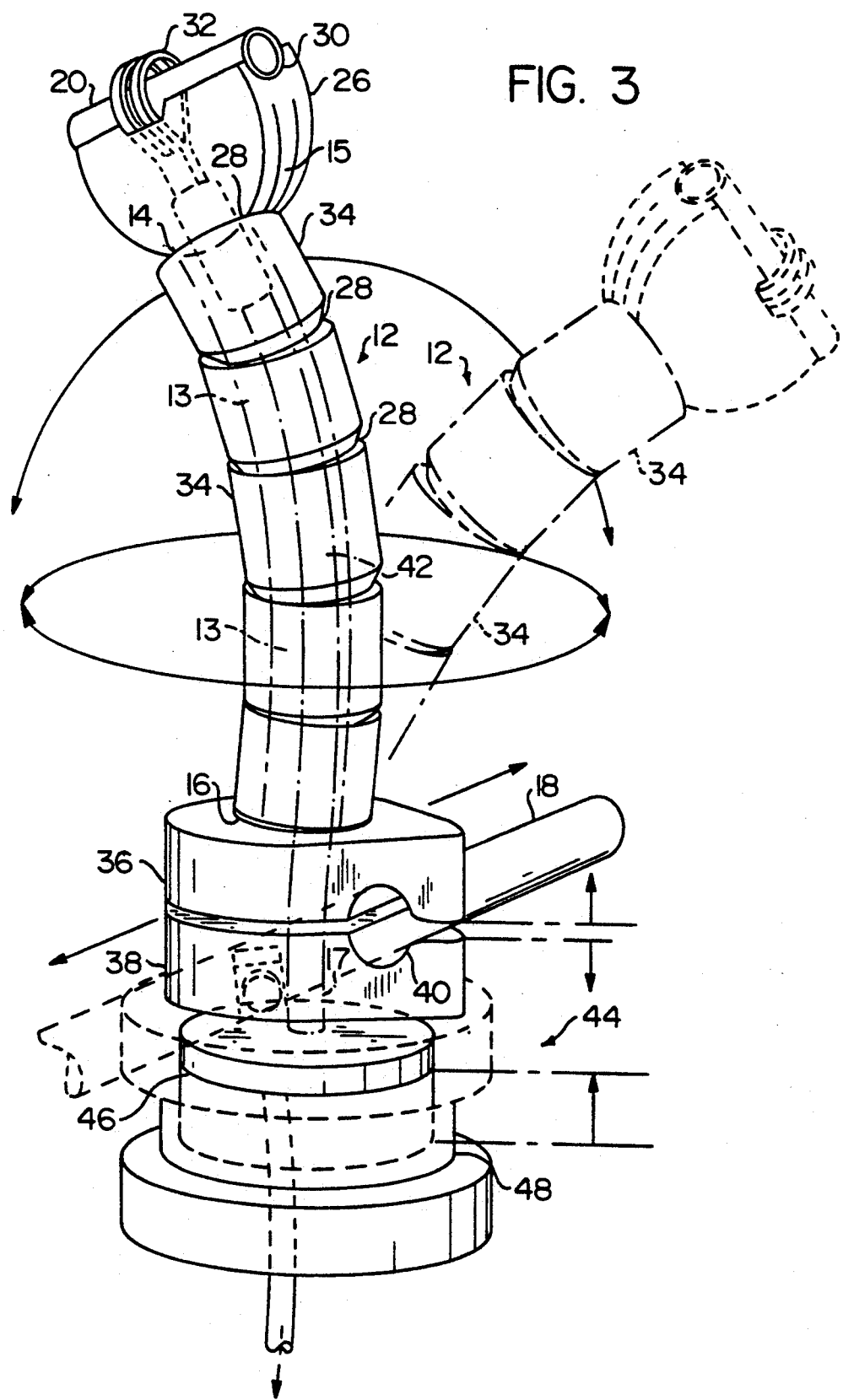
FIG. 3 is a similar view of the retractor holding device shown in FIG. 2 in its uncompressed or relaxed state.

In one preferred embodiment as shown in FIGS. 2 and 3, column 12 may preferably comprise a plurality of stacked segments 34. Segments 34 are freely rotatable relative each other with frictional interfaces 28 between each segment. A basic ball joint or socket device may be employed to establish frictional interfaces 28. Segments 34 may be generally hollow, defining path 13 through column 12. Segments 34 are designed to be freely rotatable relative each other thereby giving column 12 the overall capability of being shaped or bent into any desired posture. Upon being compressed or pushed together, segments 34 securely bind against each other. In other words, frictional interfaces 28 between segments 34 become non-moveable. The compression force causes the friction between segments 34 to become so great that frictional interfaces 28 "bind." Thus, segments 34 become "locked" or secured relative each other.

Flexible column 12 may comprise, for example, a laminated spring or collar type device capable of assuming a rigid posture upon being compressed. Any like type of column may be employed as flexible column 12 and is within the scope of the present invention.

In further accordance with the present invention, instrument gripping means are provided pivotally mounted to one end of the flexible column. As embodied herein and shown for examples in FIGS. 2 and 3, the instrument gripping means may comprise pivotal head 26 having pivotal frictional interface 28 with flexible column 12. Pivotal head 26 further defines recessed instrument seating surface 30 within which surgical instruments are positioned or carried. Pivotal head 26 also defines opening 15 generally therethrough.

The concept of frictional interface 28 existing between pivotal head 26 and the last or uppermost segment 34 of flexible column 12 is essentially the same as frictional interface 28 existing between individual segments 34. For example, pivotal head 26 may comprise a relatively hard semi-circular component which slides within a recessed surface within segment 34. Pivotal head 26 may just as easily comprise a ball or circular element. Upon being compressed against the last segment 34 of column 12, frictional interface 28 binds becoming non-moveable and thereby securing pivotal head 26 relative to flexible column 12 at some predetermined attitude or angle.

The instrument gripping means further comprises clamping device 32, as shown in FIGS. 2 and 3. Clamping device 32 extends generally into pivotal head 26 through opening 15. Clamping device 32 is designed to secure surgical instrument 20 in place within recessed instrument seating surface 30 of pivotal head 26. Any conventional mechanical clamping device such as a band, an arm, or the like may be employed as clamping device 32.

In further accordance with the present invention, locking means are provided pivotally mounted to the other end of the flexible column. As embodied herein and shown for example in FIGS. 2 and 3, the locking means may comprise a segmented device having upper portion 36 and lower portion 38 and further defining path 17 therethrough. Portions 36 and 38 respectively further define recessed groove 40 through which may be disposed a positioning bar or rail. As shown in FIG. 1, positioning bar 18 may comprise any conventional tube or rail attached to the operating table. Alternatively, positioning bar 18 may comprise a portion of the operating table structure. When portions 36 and 38 are in an uncompressed state, the locking means may slide along positioning bar 18. When portions 36 and 38 are compressed together, they lock upon positioning bar 18. In this way, the locking means becomes non-moveable relative positioning bar 18.

As illustrated in FIGS. 2 and 3, flexible column 12 is pivotally mounted upon upper portion 36. More precisely, the bottom most segment 34 of column 12 has pivotal frictional interface 28 between it and upper portion 36. This arrangement allows segment 34 to be pivoted relative to upper portion 36 thereby giving flexible column 12 a far greater degree of curvature or range with respect to the locking means. This feature is illustrated particularly in FIG. 3. Flexible column 12 is freely rotatable relative to the locking means while simultaneously having the ability to assume any curvature and any angle relative to upper portion 36. Thus, flexible column 12 with the attached instrument gripping means can assume an infinite number of positions and postures relative to the locking means and anywhere along positioning bar 18.

In further accordance with the present invention, tensioning means are provided for compressing the instrument gripping means, the flexible column, and the locking means together. As embodied herein and shown for example in FIGS. 2 and 3, the tensioning means run generally through instrument gripping means opening 15, flexible column path 13, and locking means path 17. In the normal state of the tensioning means, the instrument gripping means securely grips and holds surgical instrument 20 at some predetermined attitude, flexible column 12 rigidifies in some predetermined posture, and the locking means maintains a preselected position along positioning bar 18.

As illustrated in FIGS. 2 and 3, the tensioning means may preferably comprise cable 42 having one end thereof attached to clamping device 32 through pivotal head opening 15. Cable 42 is disposed through flexible column path 13 and locking means path 17. The tensioning means according to the present invention further includes piston assembly 44 mounted to the locking means, as shown in FIGS. 2 and 3. Piston assembly 44 includes piston 46 within cylinder 48. The end of cable 42 running through the locking means is attached to piston 46. Piston assembly 44 can comprise any conventional piston arrangement.

According to the present invention, the tensioning means may also comprise pressure source 50, as illustrated in FIG. 1. Pressure source 50 is in communication with the top of piston 46 through, for example, tubing or appropriate flexible piping. In one preferred embodiment, pressure source 50 comprises a pressurized gas source, for example an operating room service pressurized air system. Hospital operating rooms are generally equipped with a service pressurized air system that operates at approximately 50 psi. This air system is well suited to be mated to the present invention as pressure source 50.

In the normal state of apparatus 10, pressure source 50 is directed to the top of piston 46 so that upon pressurization from pressure source 50, a pressurized medium such as pressurized air or gas is directed to the top of piston 46. The pressurized medium forces piston 46 to travel down within cylinder 48 to the limits of cylinder 48, a distance sufficient for causing the instrument gripping means, flexible column 12, and the locking means to be pulled together. In its relaxed or uncompressed state, the pressurized air is vented from the top of piston 46 and apparatus 10 can be moved easily along positioning bar 18, with flexible column 12 being relatively flaccid, as illustrated in FIG. 3.

Since cable 42 is attached to piston 46, the downward motion of piston 46 pulls cable 42 taut. This action, in turn, pulls clamping device 32 towards pivotal head 26, thereby securing surgical instrument 20 within recessed instrument seating surface 30. Clamping device 32 is in physical contact with pivotal head 26 and causes pivotal head 26 to compress against the uppermost stacked segment 34 of flexible column 12. Thus, pivotal head 26 is non-movably secured relative to uppermost segment 34 at some predetermined attitude or pivotal position. Stacked segments 34 of flexible column 12 are in turn compressed against each other and become non-movably fixed relative each other, as explained above. Hence, flexible column 12 assumes a predetermined rigid posture according to however the surgeon arranges flexible column 12 prior to cable 42 being pulled taut by piston 46. The bottom most segment 34 of flexible column 12 compresses against upper portion 36 of the locking means causing portions 36 and 38 to clamp together. This action forces the locking means to firmly and non-movably grasp positioning bar 18 so that the locking means are fixed relative positioning bar 18.

The pressurized medium from pressure source 50 is also ventable from cylinder 48. Upon venting the pressurized medium from cylinder 48, piston 46 is free to travel within cylinder 48 and apparatus 10 assumes a relaxed or uncompressed state. The pressurized medium need not be totally vented, but only so much as necessary to relieve the tension on cable 42.

In further accordance with the present invention, an actuation device is provided in operative communication with the tensioning means for controlling the tensioning means. As embodied herein and shown for example in FIG. 1, actuation device 22 may preferably comprise foot pedal 52 in operative communication with gas valve 54. Actuation device 22 may just as well comprise a hand lever or other manual device. Gas valve 54 may comprise any conventional type of gas valve. Foot pedal 52 is mechanically linked to gas valve 54 so that in its normal, or uncompressed state, foot pedal 52 directs gas valve 54 to transport the pressurized medium from pressure source 50 to the top of piston 46. Subsequently, upon depressing foot pedal 52, the surgeon aligns gas valve 54 to vent the pressurized medium from cylinder 48. This arrangement is preferred in that the surgeon need only manually depress foot pedal 52 to reposition the surgical instruments. Once the instruments are in the desired position, the surgeon releases foot pedal 52 and is then free to move about the operating room, with the instruments being securely positioned by apparatus 10.

In further accordance with the objects of the present invention, an apparatus for selectively positioning a surgical instrument relative to an operating table is provided. As embodied herein and shown for example in FIG. 1, apparatus 10 may comprise positioning bar 18 which is capable of being disposed generally around an operating table. Positioning bar 18 may comprise any type of rigid support structure, such as a bar or rod. In the alternative, positioning bar 18 may comprise a portion of the operating table structure.

As depicted in FIG. 1, apparatus 10 may also comprise a plurality of retractor holding devices 58. Each retractor holding device 58 is slidably mounted upon positioning bar 18 so that each retractor holding device 58 may be independently positioned at a predetermined location along positioning bar 18. This preferred embodiment may be considered as a system of the apparatuses discussed above.

Each retractor holding device 58 comprises pivotally flexible column 12, as discussed above. Each retractor holding device 58 also comprises retractor gripping means 60 mounted to one end of flexible column 12 for securely holding surgical retractor 24 at some desired attitude. Retractor gripping means 60 comprises essentially the same elements of the instrument gripping means already discussed.

Each retractor holding device 58 also comprises positioning bar locking device 62 pivotally mounted to the other end of flexible column 12 for securing retractor holding device 58 to positioning bar 18 at a predetermined location. Locking device 62 comprises essentially the elements of the locking means already discussed.

Apparatus 10 of the embodiment depicted in FIG. 1 also comprises tensioning means in operative communication with each said retractor holding device 58 and at least one actuation device 22 in operative communication with the tensioning means and configured to actuate the tensioning means. These components have already been discussed.

In one preferred embodiment of apparatus 10 depicted in FIG. 1, a plurality of actuation devices 22 are provided, preferably one such device per each retractor holding device 58. However, in an alternative preferred embodiment, one actuation device 22 may be provided to control a plurality of retractor holding devices 58. In this embodiment the surgeon could control any number of the devices by operating a single foot pedal 52. It should be apparent that any combination of foot actuation devices can be employed with any combination of retractor holding devices 58.

It will be apparent to those skilled in the art that various modifications and variations can be made to the components of the apparatus of the present invention and in the particular arrangement of the apparatuses with respect to an operating table without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. An apparatus for selectively positioning a surgical instrument relative to an operating table, the apparatus comprising:

an actuable compressible flexible column having opposite ends, said column in an unactuated state rigidifying in the desired posture;

an actuable instrument gripping member pivotably mounted to one end of said flexible column so that a frictional interface exists between said instrument gripping member and said flexible column, said instrument gripping member in an unactuated state being configurable into any desired attitude relative said flexible column and in an actuated state rigidifying relative said flexible column;

said gripping member further comprising an actuable instrument clamping device for allowing a surgical instrument to be held thereby and to be repositioned relative to said gripping member in an unactuated state and in an actuated state securely clamping a surgical instrument relative to said gripping member;

an actuable locking device pivotally mounted to the other end of said flexible column so that a frictional interface exists between said locking device and said flexible column, said locking device in an unactuated state configured to slide along an operating table positioning bar and in an actuated state configured to securely clamps upon a positioning bar;

tensioning means operatively connected to said flexible column, said instrument gripping member and said locking device for simultaneously actuating said instrument gripping member, said instrument clamping device, said flexible column, and said locking device so that substantially simultaneously, said instrument gripping member and said clamping device securely grip and hold a surgical instrument at some predetermined attitude, said flexible column is compressed and assumes a rigid posture, and said locking device maintains a preselected position on an operating table positioning bar; and an actuation device in operative communication with said tensioning means for controlling said tensioning means.

2. A device as in claim 1, wherein said instrument gripping member is configured to hold a surgical retractor.

3. A device as in claim 1, wherein said instrument gripping member comprises:

a pivotal head having a pivotal frictional interface with said flexible column and defining a recessed instrument seating surface within which surgical instruments can be carried;

said clamping device adapted for securing a surgical instrument within said recessed seating surface, and being physically connected with said tensioning means; and wherein upon actuation of said tensioning means said clamping device non-movably secures a surgical instrument against said pivotal head with said pivotal head in turn being non-movably secured at a predetermined attitude against said flexible column, said flexible column in turn being compressed so as to rigidify in position, and said locking device being compressed so as to lock into position along a positioning bar running therethrough.

4. A device as in claim 1, wherein said flexible column comprises a plurality of stacked segments with freely rotatable frictional interfaces between each said segment so that each said segment is freely rotatable relative an adjacent said segment, said segments further configured sot hat upon being compressed together said segments non-movably secured against each other causing said flexible column to rigidify in a predetermined desired posture.

5. A device as in claim 1, wherein said locking device comprises an upper portion and a lower portion, each said portion defining a recessed groove therein configured for receiving an operating table positioning bar so that said locking device in an unactuated state may slide along the positioning bar and wherein in an actuated state, said upper portion and said lower portion non-movably secure upon the positioning bar and secure said locking device at a predetermined location relative to the operating table.

6. A device as in claim 1, wherein the device further comprises a path through said flexible column, an opening in said instrument gripping member, and a path through said locking device, and wherein said tensioning means comprises:
- a cable with one end thereof operatively attached within said instrument gripping member to said clamping device, said cable running through said flexible column and said locking device;
- a piston assembly mounted to said locking device, said piston assembly including a piston within a cylinder the other end of said cable being attached to said piston; and
- a pressure source disposed in communication with the top of said piston so that upon pressurization from said pressure source, said piston is forced to travel within said cylinder and thereby pulls said clamping device, said instrument gripping member, said flexible column, and said locking device together, and so that upon venting said cylinder, said clamping device, said gripping member, said flexible column, and said locking device are permitted to separate from each other and assume their unactuated states.

7. A device as in claim 6, wherein said pressure source comprises a pressurized gas source.

8. A device as in claim 7, wherein said pressurized gas source comprises an operating room service pressurized air system.

9. A device as in claim 6, wherein said actuation device comprises a foot pedal in operative communication with a gas valve, said gas valve being configured to direct pressurized gas from said pressure source into communication with the top of said piston when said foot pedal is not actuated, and to vent the pressurized gas from said cylinder when said foot pedal is actuated.

10. An apparatus for selectively positioning a surgical instrument relative to an operating table, the apparatus comprising:
- a positioning bar capable of being disposed generally around an operating table;
- a plurality of retractor holding devices, each said retractor holding device slidably mounted upon said positioning bar so that each said retractor holding device may be positioned at a predetermined location along said positioning bar, each said retractor holding device further comprising:
  - an actuable pivotally flexible column;
  - an actuable retractor gripping member pivotally mounted to one end of said flexible column for holding a surgical retractor at some desired attitude relative said flexible column;
  - an actuable surgical instrument clamping device operatively communicating with said gripping member adapted to releasably secure a surgical retractor relative to said gripping member; and
  - an actuable positioning bar locking device pivotally mounted to the other end of said flexible column for securing the retractor holding device to said positioning bar at a predetermined location;
- tensioning means in operative communication with each said retractor holding device for simultaneously actuating said flexible columns, said retractor gripping members, said clamping devices, and said positioning bar locking devices of said retractor holding devices so that in a simultaneous action each of said flexible columns rigidify in some predetermined posture, each of said retractor gripping members maintain a separate surgical retractor at a predetermined attitude, each of said clamping devices clamp a retractor relative said gripping members and each of said positioning bar locking devices lock their associated said retractor holding device at some predetermined position along a positioning bar; and
- at least one manual actuation device in operative communication with said tensioning means for controlling said tensioning means.

11. An apparatus as in claim 10, wherein said apparatus further comprises a path through said flexible column and a path through said positioning bar locking device, said path through said positioning bar locking device being in communication with said path through said flexible column, and wherein said tensioning means includes a piston assembly for each said retractor holding device, said piston assembly comprising a piston within a cylinder, a cable connected between said piston and said retractor gripping member through said flexible column and said positioning bar locking device, and a single pressurized gas source directed to the top of each said piston.

12. An apparatus as in claim 11, wherein said manual actuation device further comprises a pedal operatively connected to a gas valve, said gas valve being configured to direct pressurized gas from said pressurized gas source to the top of each said piston when said pedal is in a first position, and to vent the pressurized gas from each said piston when said pedal is placed in a second position.

13. An apparatus as in claim 12, further comprising a plurality of said manual actuation devices wherein one said actuation device operates with one said retractor holding device.

14. A surgical retractor positioning and securing device for selectively positioning a retractor at a predetermined location around an operating table and at some predetermined attitude relative the operating table, comprising:
- an operating table positioning bar configured to be disposed generally around an operating table;
- a positioning bar locking device slidably mountable upon said positioning bar, said positioning bar locking device defining a passage therethrough;
- a compressible flexible column with one end thereof pivotally mounted upon said positioning bar locking device, said flexible column including a plurality of generally hollow stacked segments with pivotal frictional interfaces therebetween so that each said segment is freely rotatable relative an adjacent said segment, said segments further configured so that upon being compressed together said segments non-movably secure against each other causing said compressible flexible column to rigidify in a predetermined posture;
- a pivotal head pivotably mounted to the other end of said flexible column with a frictional interface therebetween, said pivotal head defining a recessed retractor seating surface, said seating surface configured to receive a retractor, said pivotal head further defining an operating therethrough;
- a retractor clamping device extending from said pivotal head opening, said retractor clamping device configured to securely hold a retractor against said pivotal head within said recessed retractor seating surface;

a cable having one end attached to said retractor clamping device, said cable running through the passages said pivotal head, said flexible column, and said positioning bar locking device;

a piston assembly mounted to said positioning bar locking device, said piston assembly including a piston within a cylinder, the other end of said cable attached to said piston;

a pressure source directed to the top of said piston so that upon pressurization from said pressure source, said piston is forced to travel within said cylinder simultaneously pulling together said retractor clamping device, said stacked segments, and said positioning bar locking device, and thereby locking said locking device upon said positioning bar at a predetermined location;

a foot pedal configured in operative communication with a gas valve, said gas valve configured to direct pressurized gas from said pressure source to the top of said piston when said foot pedal is in an unactuated state, and to vent the pressurized gas from said cylinder when said foot pedal is in an actuated state.

* * * * *